United States Patent [19]
Dirks

[11] Patent Number: 5,492,827
[45] Date of Patent: Feb. 20, 1996

[54] METHOD FOR THE PRODUCTION OF DOUBLE-HAPLOID CUCUMBERS

[75] Inventor: Robert Dirks, Maaseik, Belgium

[73] Assignee: Nunhems Zaden BV, Netherlands

[21] Appl. No.: 371,464

[22] Filed: Jan. 11, 1995

Related U.S. Application Data

[63] Continuation of Ser. No. 208,806, Mar. 9, 1994, abandoned, which is a continuation of Ser. No. 67,332, May 26, 1993, abandoned, which is a continuation of Ser. No. 926,147, Aug. 5, 1992, abandoned, which is a continuation of Ser. No. 453,695, Dec. 20, 1989, abandoned.

[30] Foreign Application Priority Data

Dec. 22, 1988 [DE] Germany .................. 38 43 199.8

[51] Int. Cl.[6] .............................. A01H 1/00; A01H 5/00
[52] U.S. Cl. .................. 435/240.45; 435/240.4; 435/240.49; 800/200; 800/DIG. 18; 47/58
[58] Field of Search ................ 800/200, DIG. 18; 435/240.4, 240.49, 240.45; 47/58.05, 58, 58.03

[56] References Cited

U.S. PATENT DOCUMENTS

| | | | |
|---|---|---|---|
| 4,003,156 | 1/1977 | Sibi et al. ................ | 47/58 |
| 4,672,035 | 7/1987 | Davidonis et al. ........ | 435/240 |
| 4,835,339 | 5/1989 | Evans et al. .............. | 800/200 |

FOREIGN PATENT DOCUMENTS

| | | |
|---|---|---|
| 0127313 | 12/1984 | European Pat. Off. . |
| 0171310 | 2/1986 | European Pat. Off. . |
| 0262971 | 4/1988 | European Pat. Off. . |
| 2566995 | 1/1986 | France ................ 47/58 |

OTHER PUBLICATIONS

Pijnacker et al., *Genetica* 71:137–140 (1986).
Dryanovska Feb. 21, 1985 Comptesrendusde l'Academie Bulgare des Sciences, vol. 38, No. 9, pp. 1243–1244, "Induced callus in vitro from ovaries and anthers of species of the Cucurbita family".
Kuckuck 1979 "Gartenbauliche Pflanzenzüchturg" Paul Parey, Berlin, para. 1.3.2.6., pp. 74–78 Gurken.
The Journal of Heredity, "Monoploidy in Cucumbers", Lewis E. Aalders, pp. 41–44.
HortScience, vol. 17(1), Feb. 1982, "Asexual Embryogenesis and Plantlet Development in Anther Culture of *Cucumis sativus* L", J. E. Lazarte and C. C. Sasser, p. 88.
Physiologia Plantarum, vol. 15, (1962), "A Revised Medium for Rapid Growth and Bio Assays with Tobacco Tissue Cultures", Toshio Murashige and Folke Skoog, pp. 473–497.
Moderne Methoden in der Pflanzenanalyse Bd. 6, (1963) "Kinetin and Kinetin–Like Compounds", Carlos O. Miller, pp. 194–202.
Z. Pflanzenzüchtung, 65, (1971), "In Vitro Development of Callus from the Pollen of Lolium and Hordeum", D. Clapham, pp. 285–292.
Genovesi, A. D. (1990) Biotechnolgy in Agriculture and Forestry, vol. 12 Haploids in Crop Improvement (ed. YPS Bajaj) Springer–Verlag, Sect. 5.
Chang et al (1981) Plant Science Letters 20:231–237.
Raven et al (1976) Biology of Plants, 2nd ed. Worth Publish Inc. NY, N.Y. p. 486.
Poehlman (1987) in Breeding Field Crops., 3rd ed., AVI Publ. Westport, Conn. pp. 148–170.
Ziv, M., et al. (1986) *Plant Science,* 47 (1986) 115–122.
Magoon, M. L., et al., (1963) "Haploids" Caryologia, vol. 16, No. 1, pp. 191–235.

*Primary Examiner*—David T. Fox
*Assistant Examiner*—Elizabeth F. McElwain
*Attorney, Agent, or Firm*—Curtis, Morris & Safford

[57] ABSTRACT

Obtaining double-haploid cucumber plants from haploid plants is considerably improved when immature or unfertilized ovulae or embryo sac cells, which may be contained in ovarial tissue, are isolated, the formation of callus, embryos or shoots is induced on a hormone-containing medium, these haploid plants are cultured and duplication of the genome is effected.

7 Claims, No Drawings

METHOD FOR THE PRODUCTION OF DOUBLE-HAPLOID CUCUMBERS

This application is a continuation of application Ser. No. 08/208,806, filed Mar. 9, 1994, now abandoned, which in turn is a continuation of application Ser. No. 08/067,332, filed May 26, 1993, now abandoned, which in turn is a continuation of 07/926,147 filed Aug. 5, 1992, now abandoned, which in turn is a continuation of 07/453,695 filed Dec. 20, 1989, now abandoned.

BACKGROUND OF THE INVENTION

The invention relates to a microbiological method for producing double-haploid Cucumis sativus plants by culturing haploid plants, which is substantially more effective than the previously known methods.

It is known that haploids are spontaneously formed in cucumbers at low frequencies, less than one haploid embryo usually being formed per thousand seeds (Aalders 1958; J. Hered. 49, 41–44). This frequency occurs in many plants, but it is not enough for application in breeding methods.

It is furthermore known (Truong-André, 1988; Proceedings of the Eucarpia congress on cucurbitaceae, Avignon-Montfavet May 31–Jun. 1–2, 1988) to grow haploid cucumbers in vitro from extracted unfertilized ovules 2–6 weeks after the female flowers have been pollinated with irradiated pollen (400–600 gy). About 3 viable haploid plants are obtained per 1000 ovules. Accordingly, this method, too, is of only limited value for application in breeding programs.

The seoradic formation of embryos and plants from cucumber anthers was described by Sasser and Lazarte; 1982 Hortscience 17, (1) 88, but the ploidy level was not investigated, and the plantlets were most probably formed from somatic tissue.

Callus cultures were obtained from ovaries and anthers by Dryanovska 1985; Comptes Rendus de l'Academie Bulgare des Sciences 38 (9), and diploid, aneuploid and haploid metaphases were observed. Callus formation is said to originate not only from sexual cells. However, no plants were regenerated. These observations therefore do not contribute to breeding programs.

SUMMARY OF THE INVENTION

The aim was therefore to produce haploid Cucumis sativus plants and, if required, to convert these into a double-haploid plant. This aim was achieved according to the invention by isolating immature or unfertilized ovules, embryo sac cells or ovarial tissue containing said cells, from ovaries of the female cucumber flowers, inducing the formation of callus, embryos or shoots with the aid of a hormone-containing medium, culturing these to give haploid plants, and duplication of the genome is effected by customary methods if this does not sufficiently happen spontaneously.

Accordingly, this procedure is a gynogenesis in the narrow sense without any sterile pollen being applied (induced parthenogenesis).

DETAILED DESCRIPTION OF THE PREFERRED EMBODIMENTS

Preferred embodiments of the method according to the invention are illustrated in greater detail in the following:

It is advantageous to culture embryos from ovaries or fruit tissue containing ovaries. For this purpose, the ovaries are taken from C. sativus plants which have been grown in the field or in the greenhouse, either in soil or in hydroponic culture. The stage of the ovaries can vary from immature ovaries having closed flowers to ovaries having mature open flowers or even flowers which are about to wither. The stage 1 to 3 days before the flower opens is preferred.

The ovaries obtained are decontaminated to destroy microorganisms on their surface. Customary methods can be employed for this sterilization, for example the traditional methods such as incubation in aqueous solutions of hypochlorite salts or hydrogen peroxide for various periods, depending on the sample size. The sterilant is then removed by washing or inactivated with other agents. It is possible but not necessary to remove the surrounding fruit tissue which may be damaged, e.g. by cutting away the walls of the ovaries; in general, the ovaries can be processed without further steps. For this purpose, they are cut in sections which contain one or more unfertilized ovulae. The section for this purpose can be effected in various ways, for example longitudinally or transversally.

The resulting ovary sections are now advantageously transferred to a plant culture medium containing mineral salts, vitamins, a carbohydrate source and hormones, the hormone being selected according to the sexual type of the plant to be cultured. The concentration of auxins can vary from 0 to $3 \times 10^{-5}$ M in combination with cytokinins. The concentration of cytokinins can likewise vary from 0 to $3 \times 10^{-5}$ M. Gibberellins can be added to the culture medium, but this is not necessary. It is possible to employ natural and synthetic analogs of these hormones. In a particular embodiment of the invention, coconut milk is added to the culture medium, if appropriate in combination with hormones. When the ovaries or fruit tissue containing the ovaries (e.g., ovary sections contained in fruit tissue) are parthenocarpous, the medium contains cytokinins and, when the ovaries or fruit tissue containing the ovaries (e.g., ovary sections contained in fruit tissue) are non-parthenocarpous, the medium contains auxins.

The containers with the inoculated ovary sections are now cultured in a controlled environment, the temperatures generally being between 20° and 30° C. and the light intensity being between 500 and 5000 lux. A 16-hour light/8-hour dark period and an illumination of 1000 lux with fluorescent tubes (white daylight) at a temperature of 27° C. is preferred.

After 2 weeks to 3 months, calli or embryos grow from the culture media and are then transferred to the same or a different culture medium to regenerate into fully developed plants. Most of the plants which originate from these embryos are haploid, even diploid embryos are occasionally observed which are of haploid origin. Examinations of the tissues show that the small plants are derived from embryo sac cells or at least from a megaspore after meiosis has taken place.

The embryo production rate depends on the sexual type of the donor plant and on the culture medium. The composition of the hormones in this connection is designed to suit the sexual type: to develop haploid embryos, parthenocarpous cucumbers usually require fewer auxins than the non-parthenocarpous ones. On average, one haploid embryo is obtained from two cultured ovaries in the case of parthenocarpous cucumbers. On customary culture media, these haploid embryos can develop into plants, for example on Miller medium or on Murashige-Skoog medium (1962) Physiologica Plantarum 15, 473.

Chromosome doubling can take place spontaneously or can be induced, it being possible to apply the customary methods, such as colchicin treatment. Double-haploid plants are transplanted under greenhouse conditions and incorporated into a breeding program.

The method according to the invention gives up to 80% haploid embryos, relative to transferred ovaries, depending on the geno type of the donor plant. Since one person can treat at least 300 ovaries per day, up to about 240 embryos of haploid origin can be obtained using this method. The invention therefore represents an enormous step forward for plant breeding programs.

In the Example which follows, percentages relate to the weight, unless otherwise defined.

EXAMPLE

Ovaries are isolated under aseptic conditions from flower buds about 1 to 2 days before the flowers open, and they are cultured at 27°–28° C. and 2000 Lux on the medium below:

Mineral salts:

Macrosalts and microsalts as described by Miller (Miller, C. O.: Kinetin and kinetin-like compounds (1963) in: Peach, K. and Tracey, M. V., editor: Moderne Methoden in der Pflanzenanalyse [Modern Methods in Plant Analysis], Vol. 6, 194–202, Berlin; Springer) as medium A.

FeEDTA, $1 \times 10^{-4}$ M Organic additives to the media as described by Fujii (Clapham, D. (1971) In vitro development of callus from pollen of Loliumand Hordeum, Z. Pflanzenzüchtg. [Journal of Plant Breeding], 65, 285–292) Sucrose, 30 g Thiamine hydrochloride, 9 mg/l 6-Benzylaminopurin, 0.79 mg/l Before the agar is added (0.5% Difco Bacto-Agar), a pH of 5.8 is adjusted in the medium. The medium is sterilized by autoclaving for 20 minutes at 115° C. As soon as the medium has cooled down to 55° to 45° C., it is poured into Petri dishes are used after the agar has cooled and solidified completely.

After 3–6 weeks, the haploid plants become visible and are cultured further on an analogous medium in which, however, cytokinin has been omitted.

I claim:

1. A method for producing haploid *Cucumis sativus* plants which comprises isolating a female flower part selected from the group consisting of unfertilized ovules, embryo sac cells, ovarial tissue containing unfertilized ovules and ovarial tissue containing embryo sac cells, inducing the direct formation of embryos with hormone-containing medium, culturing the embryos to give haploid plants; wherein when the female flower part is from a parthenocarpous plant, the medium contains cytokinins and, when the female flower part is from a non-parthenocarpous plant, the medium contains auxins.

2. The method as claimed in claim 1, wherein a Miller medium containing inorganic salts is used as the medium.

3. The method of claim 1 wherein the female flower part is contained in fruit tissue.

4. The method of claim 3 wherein a Miller medium containing inorganic salts is used as the medium.

5. The method of claim 1 wherein the isolating is under substantially aseptic conditions.

6. The method of claim 1 wherein the culturing is at a temperature between about 20° and about 30° C.

7. The method of claim 6 wherein the culturing is at a temperature of about 27° to about 28° C.

* * * * *